United States Patent
Osborne et al.

(10) Patent No.: US 7,445,611 B2
(45) Date of Patent: *Nov. 4, 2008

(54) HEMOSTASIS CANNULA (75) Inventors: Thomas A. Osborne, Bloomington, IN (US); Ram H. Paul, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/737,313

(22) Filed: Dec. 16, 2003

(65) Prior Publication Data

US 2004/0153021 A1   Aug. 5, 2004

Related U.S. Application Data (63) Continuation of application No. 09/845,951, filed on Apr. 30, 2001, now Pat. No. 6,663,599, which is a continuation of application No. 08/967,755, filed on Nov. 4, 1997, now abandoned, which is a continuation of application No. 08/547,441, filed on Oct. 24, 1995, now abandoned, which is a continuation-in-part of application No. 08/467,843, filed on Jun. 6, 1995, now abandoned, which is a continuation of application No. 08/196,846, filed on Feb. 15, 1994, now abandoned, which is a continuation-in-part of application No. 07/879,430, filed on May 6, 1992, now abandoned.

(51) Int. Cl.
*A61M 39/06* (2006.01)
*A61M 5/36* (2006.01)

(52) U.S. Cl. .................. 604/167.04; 604/256; 604/537

(58) Field of Classification Search .................. 604/86, 604/167.01–167.06, 236–37, 256, 537

See application file for complete search history.

(56) References Cited

U.S. PATENT DOCUMENTS

| 1,180,665 A | 4/1916 | McElroy |
| 2,546,672 A | 3/1951 | LeClair |
| 3,402,710 A | 9/1968 | Paleschuck |
| 3,853,127 A | 12/1974 | Spademan |
| 3,900,028 A | 8/1975 | McPhee |
| 3,977,400 A | 8/1976 | Moorehead |
| 4,000,739 A | 1/1977 | Stevens |
| 4,143,853 A | 3/1979 | Abramson |
| 4,177,814 A | 12/1979 | Knepshield et al. |
| 4,334,551 A | 6/1982 | Pfister |

(Continued)

FOREIGN PATENT DOCUMENTS

EP   0316096 A2   5/1989

(Continued)

*Primary Examiner*—Karin M Reichle
(74) *Attorney, Agent, or Firm*—Brinks Hofer Gilson & Lione (57) ABSTRACT

A medical instrument includes a housing having a housing member with a passage through which a catheter is inserted. A valve body is mounted in the housing and abuts the housing member at an end of the passage, and, as the catheter penetrates through the valve body, the valve body conforms to the outer wall of the catheter to maintain a fluid tight seal between the valve body and the catheter. When the valve body is unstressed before being mounted in the passage, the valve body has a first planar dimension and a second planar dimension that is less than the first planar dimension.

13 Claims, 10 Drawing Sheets

U.S. PATENT DOCUMENTS

| | | | |
|---|---|---|---|
| 4,412,836 A | 11/1983 | Brignola | |
| 4,424,833 A | 1/1984 | Spector et al. | |
| 4,430,081 A | 2/1984 | Timmermans | |
| 4,434,810 A | 3/1984 | Atkinson | |
| 4,436,519 A | 3/1984 | O'Neill | |
| 4,475,548 A | 10/1984 | Muto | |
| 4,496,348 A | 1/1985 | Genese et al. | |
| 4,610,665 A | 9/1986 | Matsumoto et al. | |
| 4,610,674 A | 9/1986 | Suzuki et al. | |
| 4,626,245 A | 12/1986 | Weinstein | |
| 4,634,432 A | 1/1987 | Kocak | |
| 4,657,772 A | 4/1987 | Kocak | |
| 4,705,511 A | 11/1987 | Kocak | |
| 4,723,550 A | 2/1988 | Bales et al. | |
| 4,752,287 A * | 6/1988 | Kurtz et al. | 604/99.02 |
| 4,755,173 A | 7/1988 | Konopka et al. | |
| 4,798,594 A | 1/1989 | Hillstead | |
| 4,809,679 A | 3/1989 | Shimonaka et al. | |
| 4,895,346 A | 1/1990 | Steigerwald | |
| 4,909,798 A | 3/1990 | Fleischhacker et al. | |
| 4,946,133 A | 8/1990 | Johnson et al. | |
| 4,960,412 A | 10/1990 | Fink | |
| 5,006,113 A | 4/1991 | Fischer | |
| 5,064,416 A | 11/1991 | Newgard et al. | |
| 5,080,654 A | 1/1992 | Picha et al. | |
| 5,092,857 A | 3/1992 | Fleishhacker | |
| 5,098,393 A | 3/1992 | Amplatz et al. | |
| 5,100,394 A * | 3/1992 | Dudar et al. | 604/537 |
| 5,104,383 A | 4/1992 | Schichman | |
| 5,106,054 A | 4/1992 | Mollenauer et al. | |
| 5,114,408 A | 5/1992 | Fleischhaker et al. | |
| 5,122,122 A | 6/1992 | Allgood | |
| 5,125,903 A | 6/1992 | McLaughlin et al. | |
| 5,154,701 A | 10/1992 | Cheer et al. | |
| 5,167,637 A * | 12/1992 | Okada et al. | 604/167.04 |
| 5,176,652 A | 1/1993 | Littrell et al. | |
| 5,178,607 A * | 1/1993 | Lynn et al. | 604/86 |
| 5,195,980 A | 3/1993 | Catlin | |
| 5,199,948 A * | 4/1993 | McPhee | 604/86 |
| 5,201,725 A | 4/1993 | Kling | |
| 5,207,656 A | 5/1993 | Kranys | |
| 5,211,633 A | 5/1993 | Stouder, Jr. | |
| 5,211,634 A | 5/1993 | Vaillancourt | |
| 5,215,537 A * | 6/1993 | Lynn et al. | 604/244 |
| 5,242,393 A * | 9/1993 | Brimhall et al. | 604/86 |
| 5,269,763 A | 12/1993 | Boehmer et al. | |
| 5,269,764 A | 12/1993 | Vetter et al. | |
| 5,273,546 A | 12/1993 | McLaughlin et al. | |
| 5,300,033 A | 4/1994 | Miller | |
| 5,300,034 A | 4/1994 | Behnke et al. | |
| 5,354,275 A * | 10/1994 | Behnke et al. | 604/86 |
| 5,395,352 A * | 3/1995 | Penny | 604/256 |
| 5,402,982 A * | 4/1995 | Atkinson et al. | 251/149.1 |
| 5,409,463 A | 4/1995 | Thomas et al. | |
| 5,441,487 A | 8/1995 | Vedder | |
| 5,456,284 A | 10/1995 | Ryan et al. | |
| 5,540,661 A | 7/1996 | Tomisaka et al. | |
| 5,578,059 A | 11/1996 | Patzer | |
| 5,599,327 A | 2/1997 | Sugahara et al. | |
| 5,657,963 A | 8/1997 | Hinchliffe et al. | |
| 6,024,729 A | 2/2000 | Dehdashtian et al. | |
| 6,053,861 A | 4/2000 | Grossi | |
| 6,171,287 B1 | 1/2001 | Lynn et al. | |
| 6,200,262 B1 | 3/2001 | Ouchi | |
| 6,221,050 B1 | 4/2001 | Ishida | |
| 6,228,060 B1 | 5/2001 | Howell | |
| 6,261,266 B1 * | 7/2001 | Jepson et al. | 604/201 |
| 6,261,282 B1 | 7/2001 | Jepson et al. | |
| 6,287,280 B1 | 9/2001 | Lampropoulous et al. | |
| 6,344,033 B1 | 2/2002 | Jepson et al. | |
| 6,416,499 B2 | 7/2002 | Paul, Jr. | |
| 6,488,674 B2 | 12/2002 | Becker et al. | |
| 6,506,181 B2 | 1/2003 | Meng et al. | |
| 6,520,939 B2 | 2/2003 | Lafontaine | |
| 6,575,960 B2 | 6/2003 | Becker et al. | |
| 6,595,964 B2 | 7/2003 | Finley et al. | |
| 6,632,200 B2 | 10/2003 | Guo et al. | |
| 6,663,599 B2 * | 12/2003 | Osbourne et al. | 604/167.04 |
| 6,669,681 B2 | 12/2003 | Jepson et al. | |
| 2001/0020153 A1 | 9/2001 | Howell | |
| 2001/0021825 A1 | 9/2001 | Becker et al. | |
| 2001/0041872 A1 | 11/2001 | Paul, Jr. | |
| 2002/0010425 A1 | 1/2002 | Guo et al. | |
| 2002/0010436 A1 | 1/2002 | Becker et al. | |
| 2003/0014015 A1 | 1/2003 | Tansey, Jr. et al. | |
| 2004/0006330 A1 | 1/2004 | Fangrow, Jr. | |

FOREIGN PATENT DOCUMENTS

| | | |
|---|---|---|
| WO | WO91/10459 | 7/1991 |
| WO | WO95/21642 | 8/1995 |
| WO | WO97/15338 | 5/1997 |

* cited by examiner

HEMOSTASIS CANNULA

RELATED APPLICATIONS

This application is a continuation at U.S. application Ser. No. 09/845,951 filed Apr. 30, 2001, which issued as U.S. Pat. No. 6,663,599 on Dec. 16, 2003, which is a continuation of U.S. application Ser. No. 08/967,755, filed Nov. 4, 1997, now abandoned, which is a continuation of U.S. application Ser. No. 08/547,441, filed Oct. 24, 1995, now abandoned, which is a continuation-in-part of U.S. application Ser. No. 08/467,843, filed Jun. 6, 1995, now abandoned, which is a continuation of U.S. application Ser. No. 08/196,846, filed Feb. 15, 1994, now abandoned, which is a continuation-in-part of U.S. application Ser. No. 07/879,430, filed May 6, 1992, now abandoned.

The entire contents of the above applications are incorporated herein by reference.

BACKGROUND OF THE INVENTION

This invention relates to a cannula or sheath and particularly to a cannula useful with angiographic catheters.

In certain angiographic studies, the angiographer uses the Desilets-Hoffman procedure to do a multiple study. In this procedure, the angiographer obtains access to a patient's blood vessel by inserting a hollow needle through the skin and into the lumen of the blood vessel. A guide wire is passed through the needle and advanced through the artery or vein into the organ to be studied. The needle is removed leaving the guide wire in the organ. A cannula and dilator are advanced over the wire into the vessel and the dilator is removed along the guide wire. The angiographer then conducts the multiple studies by inserting various types of catheters into the vessel through the cannula or sheath. In order to avoid excessive bleeding and to insure against the possibility of an air embolism, this technique requires occlusion of the passage through the cannula during catheter changes.

One method of obtaining the required occlusion is to position a valve body formed from a pliable material in the passageway of the cannula. Such valve bodies are shown for instance in U.S. Pat. No. 4,000,739 to Stevens, U.S. Pat. No. 4,430,081 to Timmermans, U.S. Pat. No. 4,610,665 to Matsumoto et al., U.S. Pat. No. 5,006,113 to Fischer and International Publication Number WO 91/10459 to Savage et al. In each of these patents, one or more disk-like gaskets are mounted in the cannula passage. The disk-like gaskets or valve bodies include an opening therethrough which is biased to a closed position when no catheter is present in order to prevent an air embolism from occurring by air being drawn into the patient's vein through the cannula. When a catheter is inserted through the valve body into the passage of the cannula, the valve body conforms to the shape of the outer wall of the catheter, thereby preventing blood flow out of the cannula between the catheter and the valve body.

BRIEF SUMMARY OF THE INVENTION

In general, the present invention is directed to a medical instrument, such as a cannula or sheath, that includes a housing having a housing member with a passage through which a catheter is inserted. A valve body is mounted in the housing and abuts the housing member at an end of the passage, and, as the catheter penetrates through the valve body, the valve body conforms to the outer wall of the catheter to maintain a fluid tight seal between the valve body and the catheter.

In certain implementations, the valve body has two opposing planar surfaces and a peripheral edge that separates the faces. A first slit opens in one of the planar faces and a second slit opens in the other planar face. Each slit extends partly through the valve body and intersects with the other slit within the valve body. The fluid tight seal between the catheter and the valve body is formed when the catheter penetrates through the intersection of the first and second slits.

In some other implementations, the valve body has a first planar face, a second planar face, and a peripheral edge that separates the faces. The valve body is also provided with a first slit that defines a first slit plane extending from the first planar face and partly through the valve body and a second slit that defines a second slit plane extending from the second planar face and partly through the valve body such that the first and second slit planes intersect within the valve body. As the catheter penetrates through the intersection between the first and second slit planes, the fluid tight seal is formed between the catheter and the valve body.

The first and second slits may be oriented at an angle with respect to each other. For example, they may be perpendicular to each other.

In any of the forgoing implementations, when the valve body is unstressed before being mounted in the housing so as to abut the housing member at an end of the passage, the valve body has a first planar dimension and a second planar dimension that is less than the first planar dimension. Thus, the peripheral edge is non-circular when the valve body is unstressed. For example, the peripheral edge can have an oval shape before the valve body is mounted in the housing.

In other implementations, the valve body has a first planar face, a second planar face, and a peripheral edge that separates the faces. The valve body is also provided with a slit that defines a slit plane extending from the first planar face and partly through the valve body and an opening extending from the second planar face and partly through the valve body such that the slit plane and the opening intersect within the valve body. The opening is provided with an internal ring positioned within the valve body between the second planar face and the intersection between the slit plane and the opening. As the catheter penetrates through the slit plane and the internal ring, the fluid tight seal is formed between the catheter and the valve body.

The housing may be provided with a recess having a dimension that is less than the first dimension of the valve body. Accordingly, the valve body is compressed along the first dimension when the valve body is received within the recess.

Other features and advantages will be apparent from the following drawings, detailed description, and claims.

DETAILED DESCRIPTION OF THE INVENTION

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
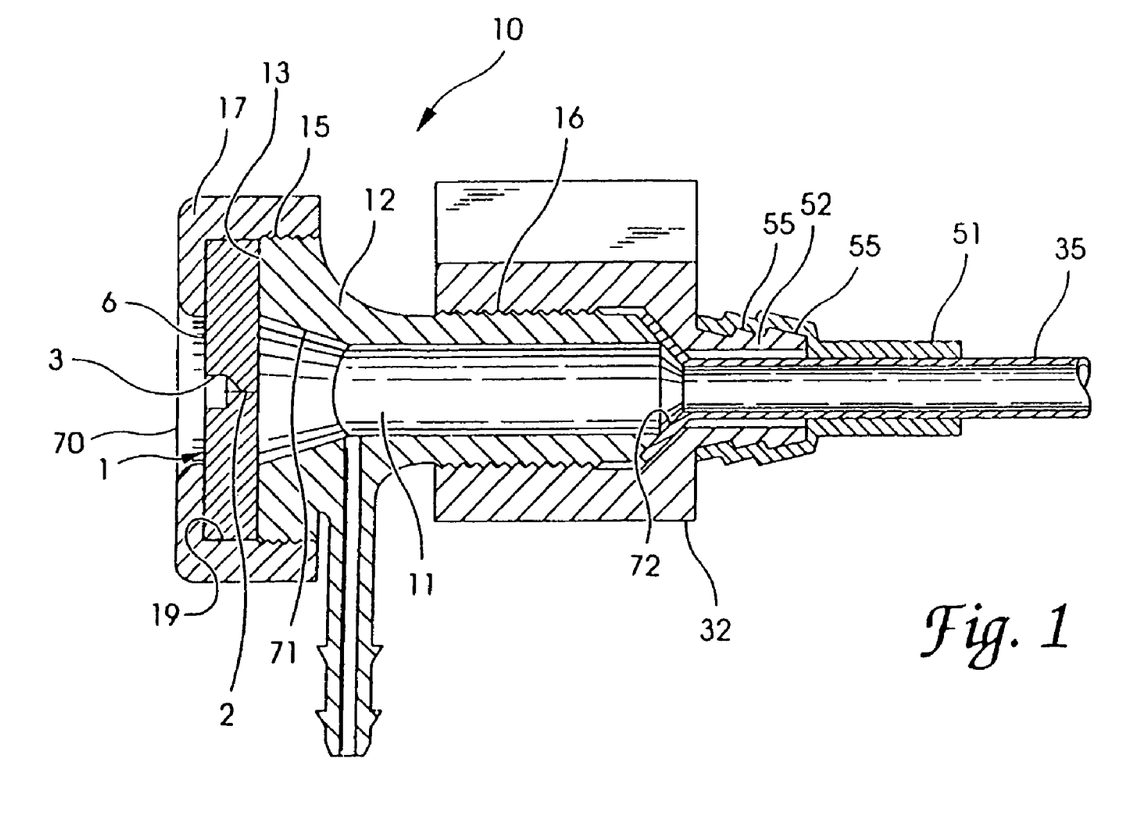
FIG. 1 is a cross-sectional view taken axially of a hemostasis cannula of one embodiment of the present invention.
Figure 2:
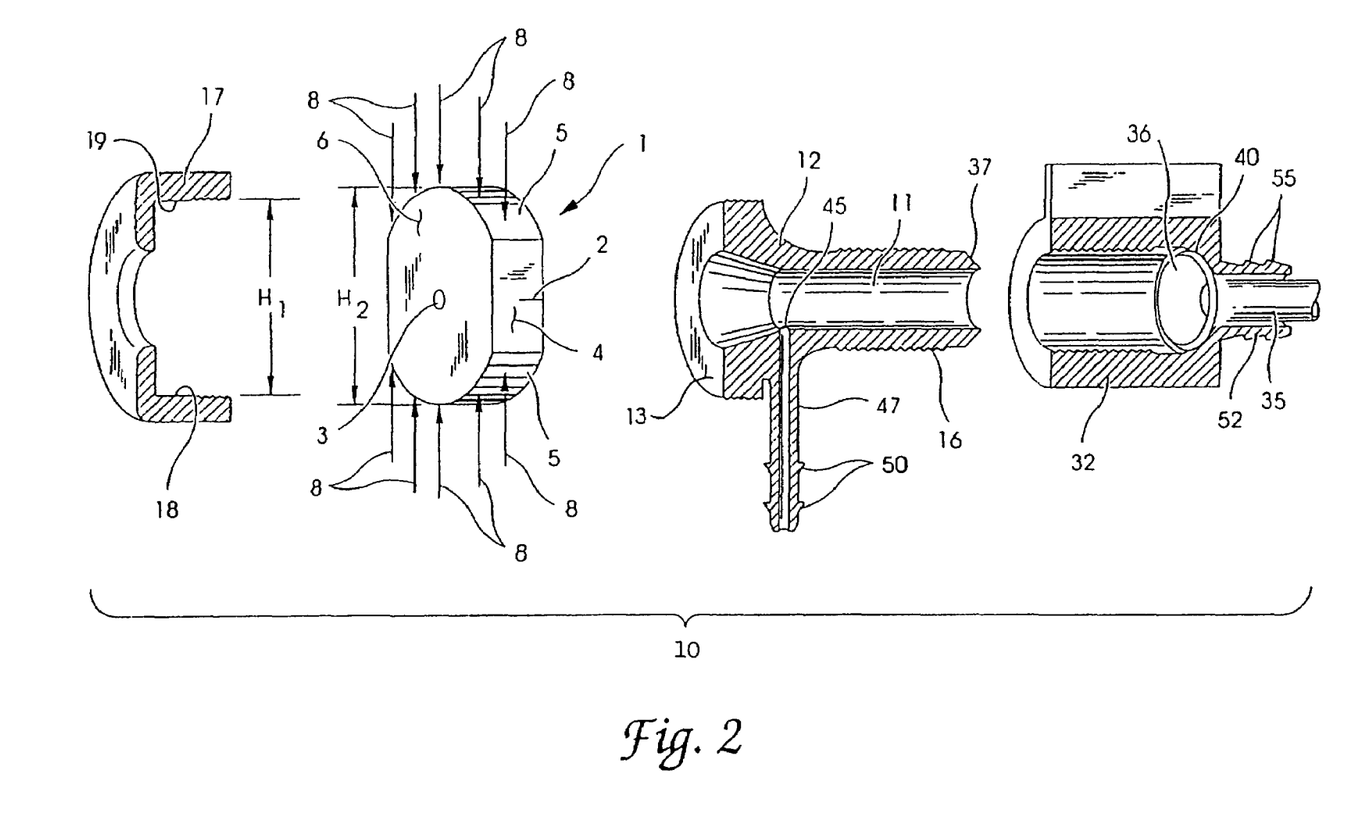
FIG. 2 is an exploded partially cut-away view of the embodiment of FIG. 1.

Referring now more particularly to the drawings, there is illustrated in FIGS. 1 and 2 a hemostasis cannula which includes a cannula housing or housing 10 having a housing member or member 12 including a passage 11 therethrough adapted to receive a catheter. Housing member 12 has an abutting surface 13 and two externally threaded surfaces 15 and 16. A cap 17, which includes recess 18 and defines an internal wall 19, is threaded down on the member 12 on the threads 15 and is glued in place by a suitable cement or the like. Valve body 1 is received into recess 18 and is sandwiched or disposed between sections of wall 19 in cap 17 and abuts housing member 12. As can be seen in FIGS. 1 and 2, the face 6 including the cylindrical recess or hole 3 of valve body 1 is directed towards the opening 70 of the cap 17.

The cannula housing 10 also includes an internally threaded member 32, the threads of which are suitable for mating engagement with the threads 16 on the member 12. The function of the member 32 is to receive and fix or hold the flexible tubing 35 to the housing 10. In the assembly procedure, adhesive or cement is placed on the flexible tubing 35 and between the members 12 and 32 for affixing the tubing and members together. The flexible tubing 35 has a flared end 36 which is fixed between the tapered surfaces 37 and 40 of the members 12 and 32.

Figure 3:
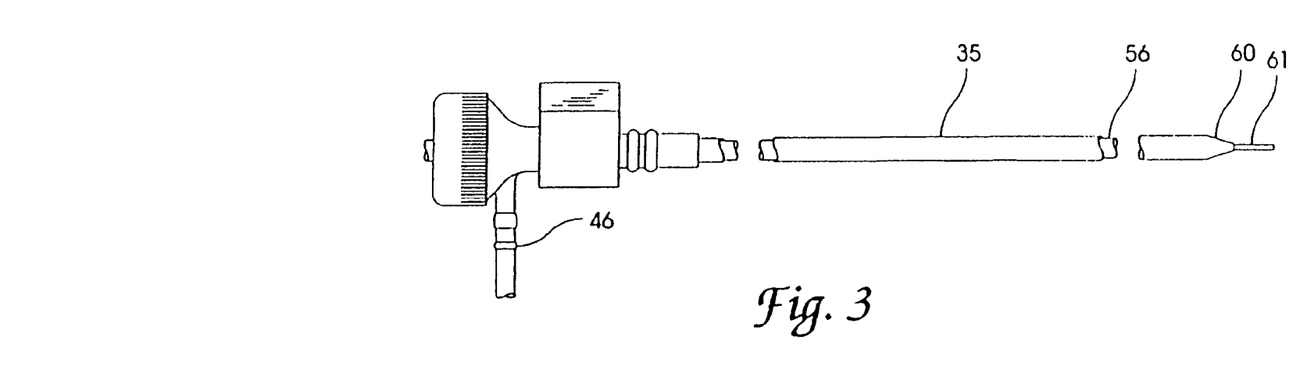
FIG. 3 is a side elevational view of the cannula having a dilator unit and wire guide therein.

Cannula housing 10 is provided with a port 45 which communicates with passage 11 between valve body 1 and flexible tube 35 for introducing fluids into the patient's blood vessel. In order to ensure that blood does not flow out the flushing port 45, the physician normally maintains a positive pressure of flushing fluid through the flexible tubing 46 (FIGS. 3 and 4), which is attached to the projection 47 by means of the annular ridges 50. The flexible tubing 35 is further secured to housing 10 by means of shrinkable tubing 51 which is secured about collar 52 via the annular ridges 55. As seen in FIG. 3, a hollow plastic dilator 56 having an outer diameter substantially equal to that of catheter 57 (FIG. 4) may be positioned in the passage 11 with the tapered end 60 of the dilator extending past the distal end of tube 35. After the cannula has been inserted into the blood vessel over the guide wire 61 and the dilator 56, the dilator 56 and guide wire 61 can be removed and discarded.

Valve body 1 is oblong in shape and has a height dimension $H_2$ which is greater than the height dimension $H_1$ of recess 18. Therefore, valve body 1 must be compressed in the direction of arrows 8 in order to be received within recess 18. Valve body 1 includes a pair of opposing faces 6 which are separated by a peripheral edge 5. A hole or cylindrical recess 3 is made through one of the faces and extends partially through the valve body as shown in FIG. 1. The hole 3 may be formed by molding during the process of forming the disk or punched, cut or drilled in a separate operation. A slit 2 is made through the other face and extends partially through the valve body intersecting hole 3 within the valve body.

Valve body 1 is preferably made from silicon rubber or another elastomer having a Durometer hardness anywhere between 20 and 90. Referring to FIGS. 5-8, valve body 1 preferably has an oblong shape such that peripheral edge 5 includes a pair of parallel planar surfaces 4 which are perpendicular to the plane defined by slit 2. Slit 2 preferably extends completely across one of the faces 6 and extends into the valve body to a depth of between ⅓ and ⅔ the thickness of the valve body. Hole 3 preferably has a diameter between 0.010 and 0.035 inches and, like slit 2, has a depth preferably between ⅓ and ⅔ the thickness of valve body 1. In any event, the combined depth of hole 3 and slit 2 must be sufficient that they intersect within the valve body and create an opening completely through the valve body for receiving a catheter or the like therethrough.

Figures 7, 8:
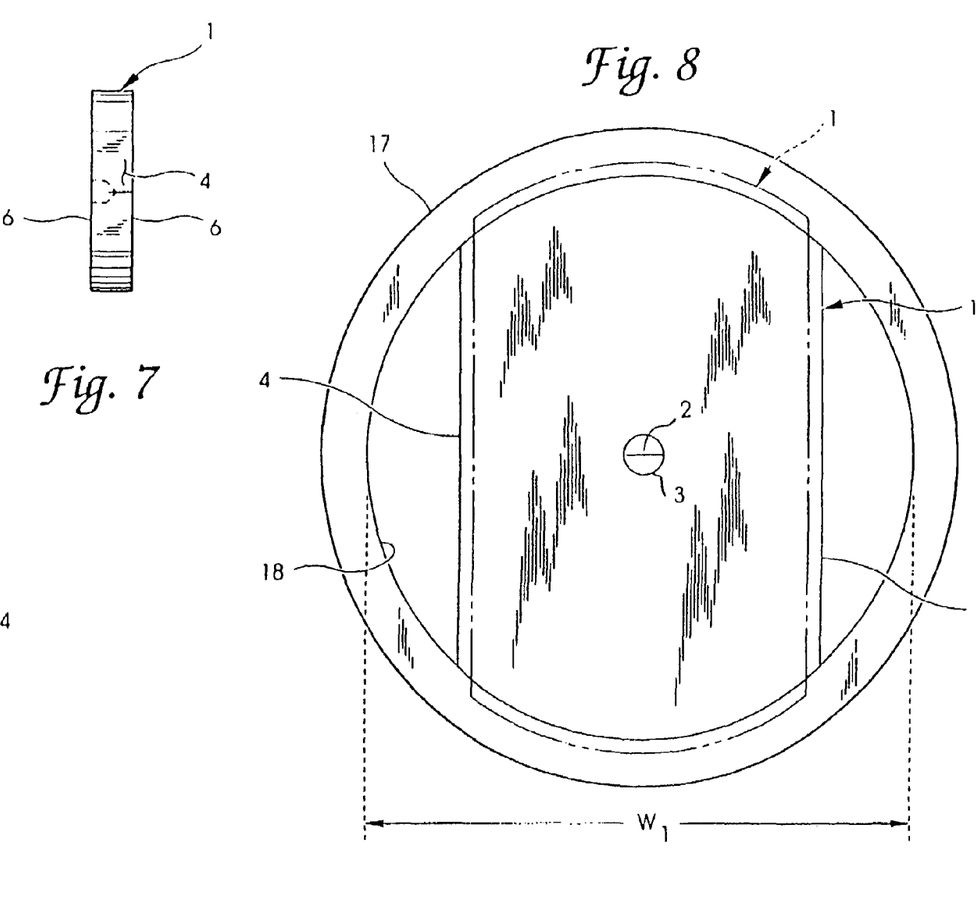
FIG. 7 is a side view of the valve body shown in FIGS. 5 and 6.
FIG. 8 is a view looking axially into the recess portion of the housing of the hemostasis cannula of the present invention showing a front view of the valve body of FIGS. 5-7 before and after it has been compressed and fitted into the recess of the housing.

Of course, the oblong shape of valve body 1 results in it having a height dimension $H_2$ which is greater than its width dimension $W_2$. FIG. 8 shows the valve body 1 both before and after it has been compressed in order to be positioned in recess 18 of housing 10. Before being compressed, valve body 1 has a height dimension $H_2$ which is greater than height dimension $H1$ of recess 18 as shown in FIG. 2. So that the compression forces on valve body 1 are directed only perpendicularly to slit 2, valve body 1 has a width dimension $W_2$ which is less than the width dimension $W_1$ of recess 18. The oblong shape of valve body 1, when assembled into the cannula, applies a slight amount of pressure perpendicular to the slit making certain it closes completely after the removal of the dilator or a catheter. Planar portions 4 allow valve body 1 to expand in its width dimension without interacting with the recess when it is compressed and received within the recess 18.

Figure 9:
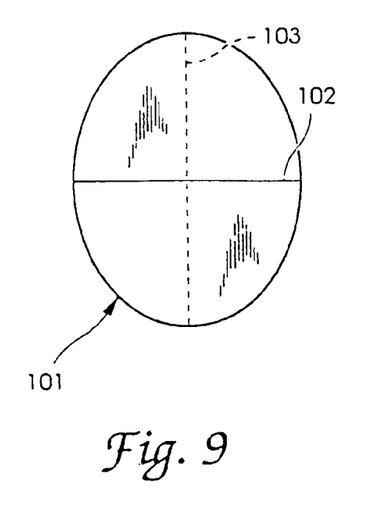
FIG. 9 is a front view of another valve body according to the present invention.
Figure 10:
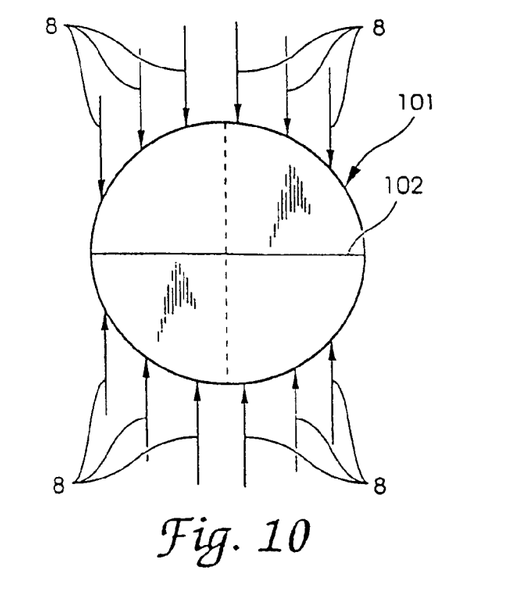
FIG. 10 is a front view of the valve body shown in FIG. 9 after being compressed.

FIGS. 9 and 10 show another embodiment of a valve body 101 which can be used with the hemostasis cannula of FIGS.

1 and 2. In this case, valve body 101 is oblong in shape and includes a pair of intersecting slits 102 and 103. The slit configuration of the valve body 101 may be as is more completely described in U.S. Pat. No. 4,610,665 to Matsumoto et al., which description is incorporated herein by reference. Alternatively, the intersecting slits 102 and 103 may extend completely across the respective faces of valve 101, as is shown in FIGS. 9 and 10. The important aspect in this case is that the oblong shape of valve body 101 is compressed along arrows 8 perpendicular to slit 102 so that the valve body may be received within the recess of a cannula housing as described previously. The compression force 8 improves the performance by insuring that slit 102 remains closed during catheter exchanges.

Figure 11:
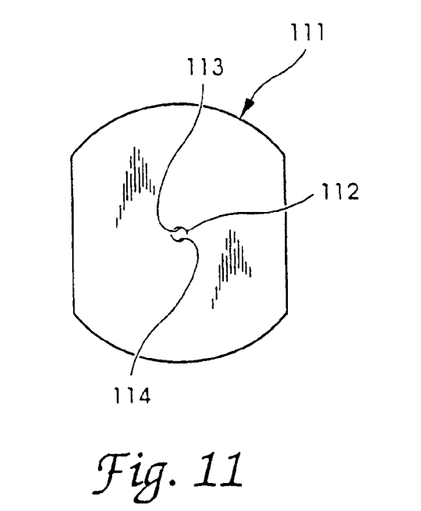
FIG. 11 is a front view of still another valve body according to the present invention.
Figure 12:
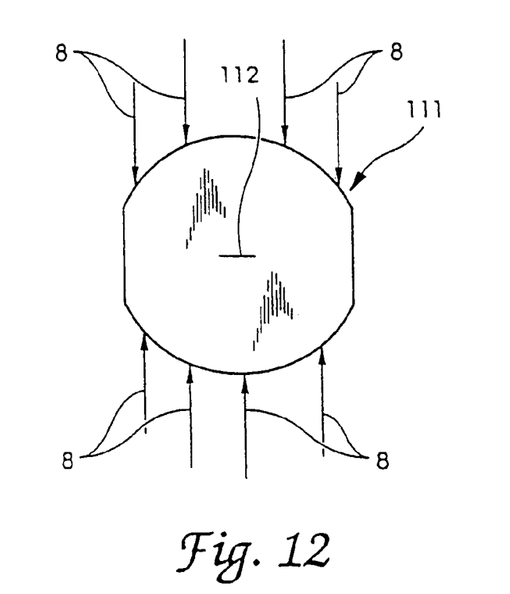
FIG. 12 is a front view of the valve body shown in FIG. 11 after being compressed.

FIGS. 11 and 12 illustrate still another embodiment of a valve body according to the present invention. In this case, valve body 111 is oblong in shape similar to the shape discussed in reference to valve body 1 shown in FIGS. 5-8. In this case, however, valve body 111 includes a hole 112 completely through the valve body. Hole 112 includes boundary walls 113 and 114 which remain separate when valve body 11 is uncompressed. When sufficient compression is applied to valve body 111, as shown in FIG. 12, boundary walls 113 and 114 are forced together, thus forming a fluid-tight seal through the valve body. Thus, the compression concept of the present invention has application in hemostasis cannulas having two or more valve body gaskets as shown in U.S. Pat. No. 4,000,739 to Stevens or U.S. Pat. No. 4,430,081 to Timmermans, or to hemostasis cannulas containing a single valve body gasket as shown in U.S. Pat. No. 4,610,665 to Matsumoto et al., and U.S. Pat. No. 5,006,113 to Fischer.

Figure 13:
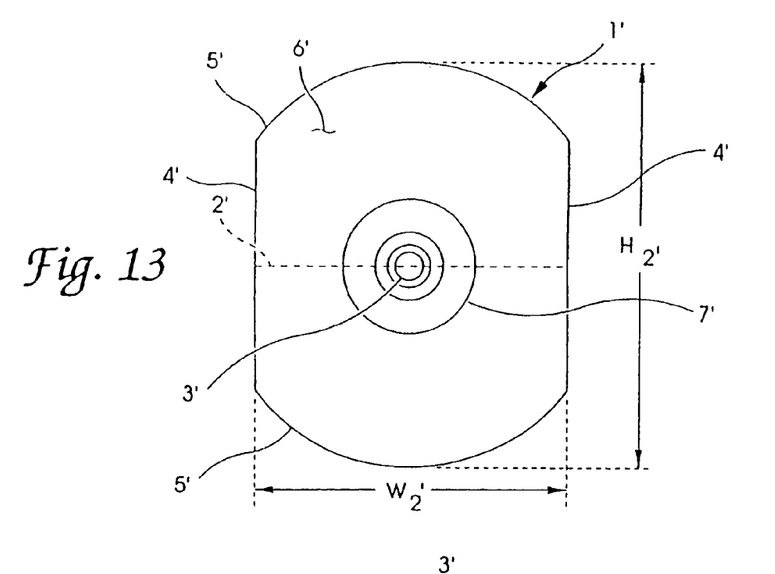
FIG. 13 is a front view of a further embodiment of a valve body used in the hemostasis cannula of FIGS. 1 and 2.

FIGS. 13-15A show yet another embodiment of a valve body according to the present invention. FIG. 13 is a front view of a valve body 1' which is substantially similar to the valve body 1, with the major difference being the addition of a raised ring or doughnut 7' which surrounds the hole 3'. The valve body 1' may be substituted for the valve body 1 in the hemostasis cannula of FIGS. 1 and 2. Likewise, the face 6' including the cylindrical recess or hole 3' and the raised ring 7' of valve body 1' may be directed towards the opening 70 of the cap 17 (FIGS. 1 and 2).

Figure 14:
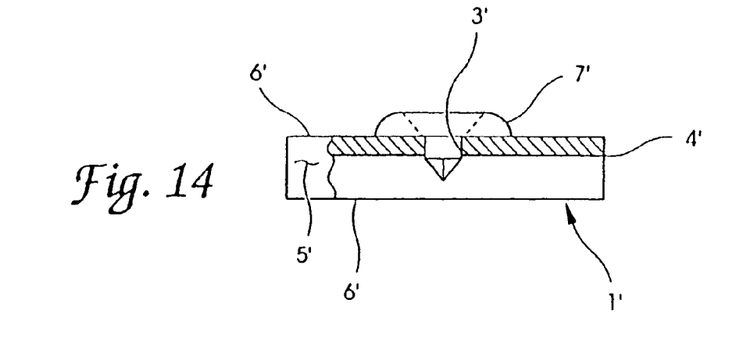
FIG. 14 is a side partially cut-away view of the valve body shown in FIG. 13.

As with valve body 1, valve body 1' is oblong in shape and has a height dimension $H_2'$ which is greater than the height dimension $H_1$ of recess 18 of FIG. 1. Therefore, valve body 1' must additionally be compressed in the direction of arrows 8 in order to be received within recess 18. Valve body 1' includes a pair of opposing planar faces 6' which are separated by a peripheral edge 5'. A hole or cylindrical recess 3' is made through one of the faces and extends partially through the valve body as shown in FIG. 14. The hole 3' may be formed by molding during the process of forming the disk or punched, cut or drilled in a separate operation. A slit 2' is made through the other face and extends partially through the valve body intersecting hole 3' within the valve body. Additionally, a raised ring 7' on the top surface of the valve provides a lead-in to the hole 3' of the valve body 1'. As such, the raised ring 7' makes it easier to place very small diameter devices through the valve. The extra material around the hole 3' additionally makes the valve less likely to tear.

Further, valve body 1' (including raised ring 7') is preferably made from silicon rubber or another elastomer having a Durometer hardness anywhere between 20 and 90. Referring now to FIGS. 13-15A, valve body 1' preferably has an oblong shape such that peripheral edge 5' includes a pair of parallel planar surfaces 4' which are perpendicular to the plane defined by slit 2'. Slit 2' preferably extends completely across one of the faces 6' and extends into the valve body to a depth of between ⅓ and ⅔ the thickness of the valve body.

In one particular embodiment of the present invention, the thickness of the valve body 1' may be 0.062 inches +/−0.002 inches and the slit depth may be between 0.040 and 0.045 inches. Hole 3' preferably has a diameter of between 0.010 and 0.035 inches and, like slit 2', has a depth preferably between ⅓ and ⅔ the thickness of valve body 1'. In any event, the combined depth of hole 3' and slit 2' must be sufficient that they intersect within the valve body and create an opening completely through the valve body for receiving a catheter or the like therethrough. Of course, the oblong shape of valve body 1' results in it having a height dimension $H_{2'}$ which is greater than its width dimension $W_{2'}$, to provide a better closing force on the slit. For example in the above mentioned particular embodiment of the present valve, height $H_{2'}$ is between 0.405 and 0.410 inches in diameter compared to a width $W_{2'}$ of between 0.340 and 0.360 inches.

The raised ring 7' is centered around the hole 3'. Additionally, as can be seen more clearly in FIG. 15A, the inner wall 9' of the raised ring 7' is sloped from the top of the raised ring 7' down to the face 6'. An angle θ can be measured between a plane parallel to the face 6' and the inner wall 9'. In the above mentioned particular embodiment angle θ is 45.degree.

Further, in that embodiment, the outer diameter of raised ring 7' is chosen to be between 0.145-0.155 inches while the inner diameter, measured at the top of the raised ring, may be between 0.080-0.095 inches in diameter. Additionally, the raised ring may extend between 0.025 and 0.030 inches above the face 6'.

Figure 15:
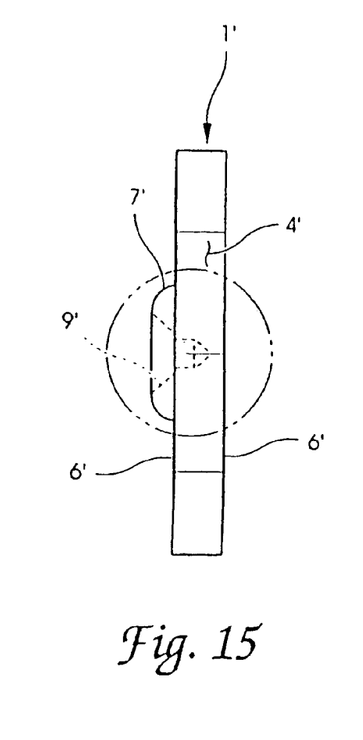
FIG. 15 is a side view of the valve body shown in FIGS. 13 and 14.
Figure 15A:
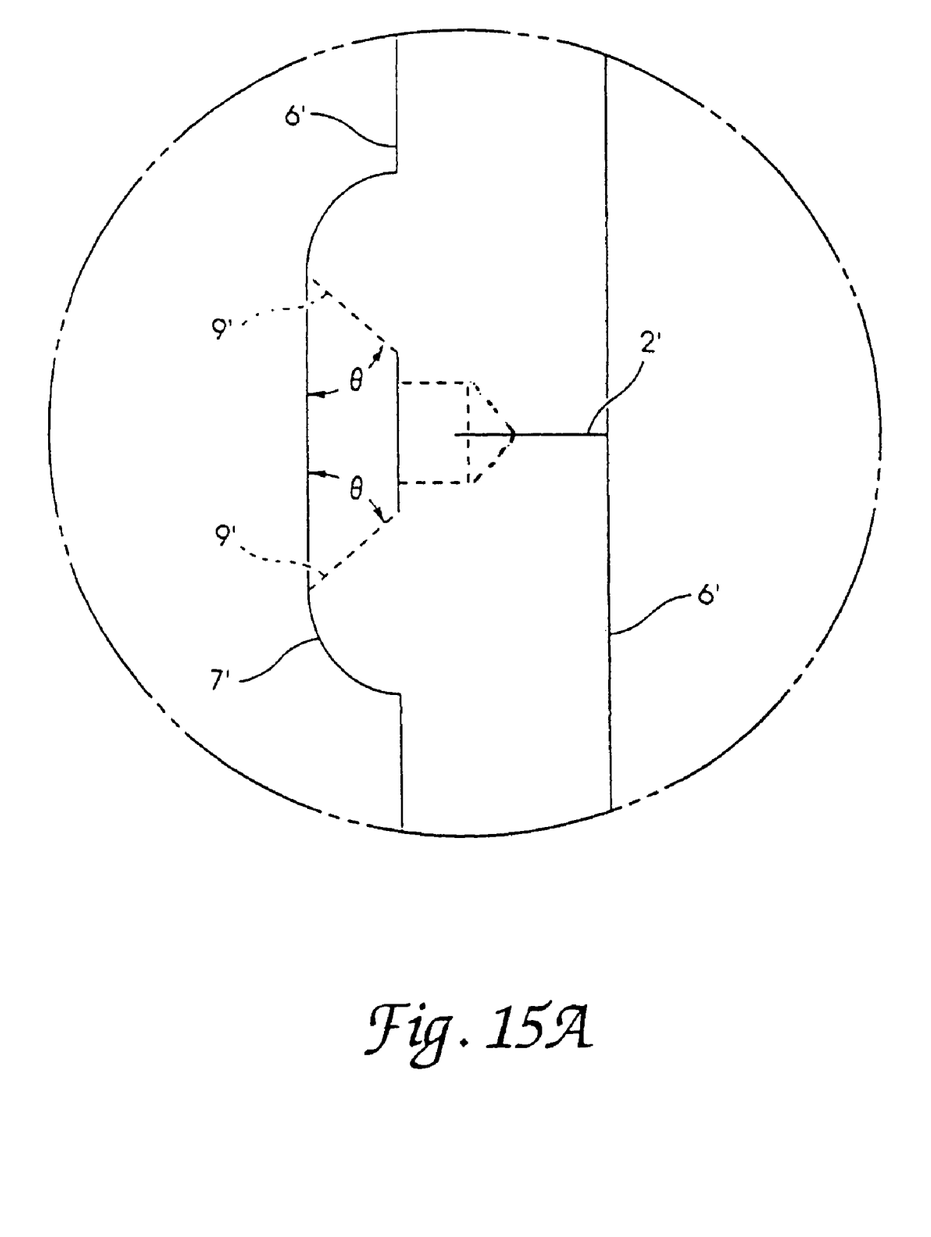
FIG. 15A is an enlarged view of a portion of the valve body shown in FIGS. 13-15.

As can be further seen in FIG. 15A, in the preferred embodiment, the tapered walls terminate at the surface of the planar face 6' prior to the beginning of the hole 3', thus forming a small planar surface between the hole 3' and the raised ring 7'. Alternately, the sloping inner wall 9' can terminate directly at the edge of the hole 3'.

As with the previous embodiments of the invention, before being compressed, valve body 1' has a height dimension $H_2$, which is greater than height dimension $H_1$ of recess 18 shown In FIGS. 1 and 2. So that the compression forces on valve body 1' are directed only perpendicularly to slit 2', valve body 1' has a width dimension $W_2$ which is less than the width dimension $W_1$ of recess 18 of FIG. 1. Planar portions 4' allow valve body 1' to expand in its width dimension without interacting with the recess when it is compressed and received within the recess 18 of FIG. 1.

Figure 16:
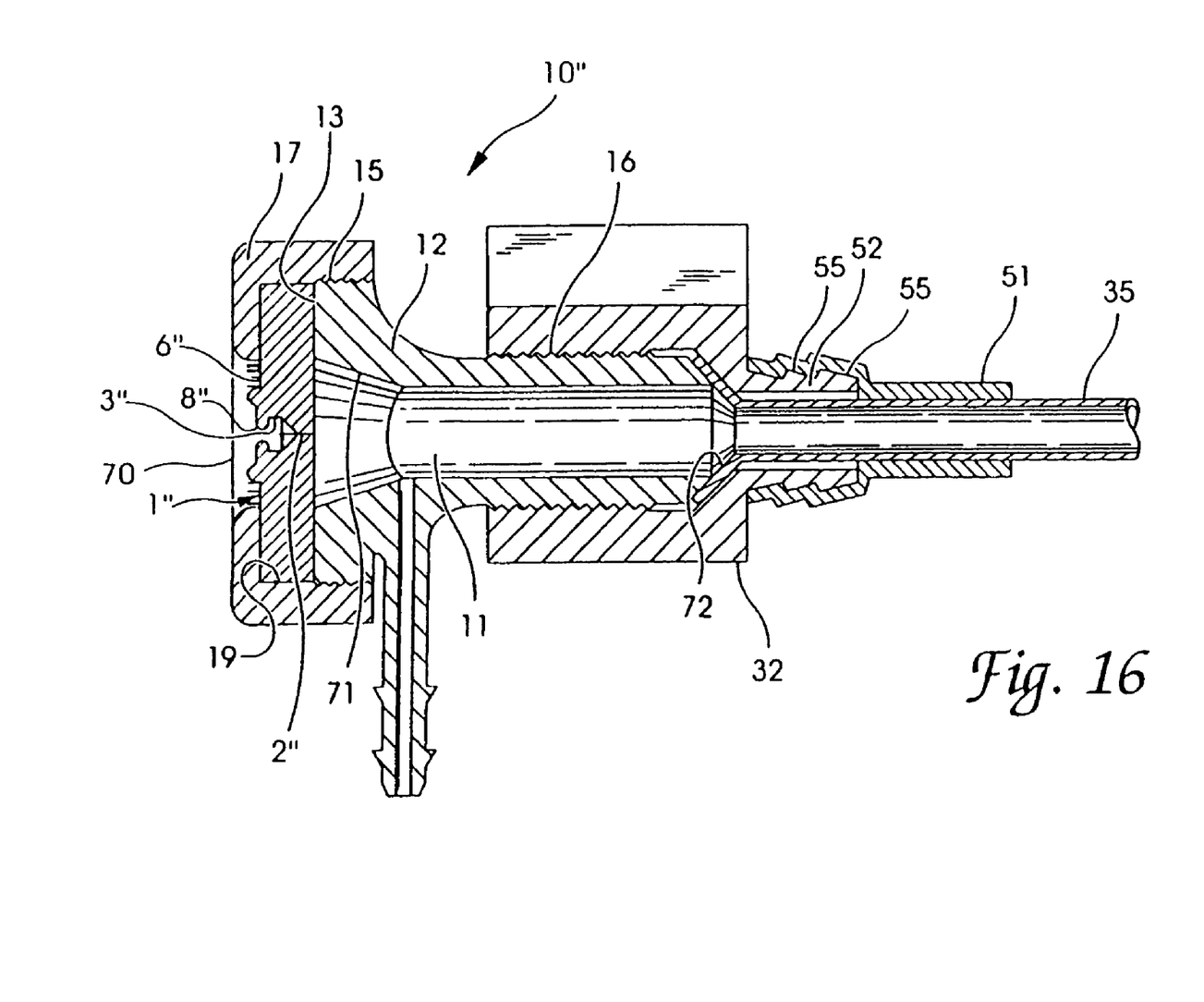
FIG. 16 is a cross-sectional view taken axially of a hemostasis cannula of another embodiment of the present invention.
Figure 17:
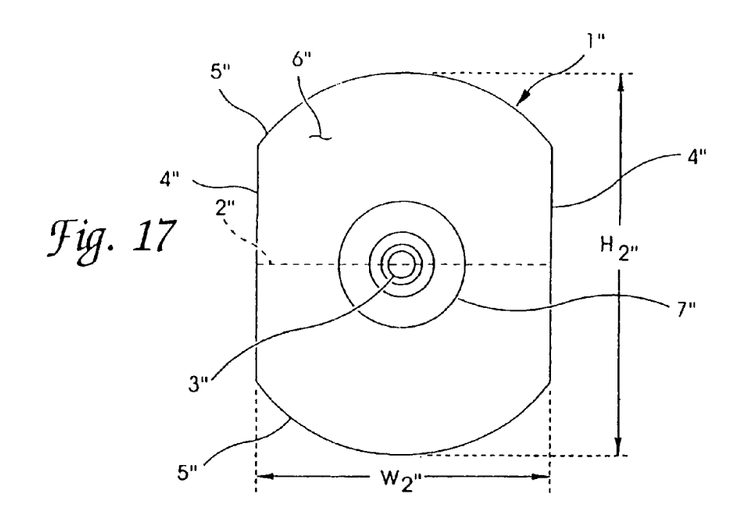
FIG. 17 is a front view of a further embodiment of a valve body used in the hemostasis cannula of FIGS. 1 and 2, as shown in FIG. 16.

FIGS. 16-19A show a further embodiment of a valve body according to the present invention. FIG. 16 is a cross-sectional view taken axially of a hemostasis cannula of another embodiment of the present invention. The hemostasis cannula of FIG. 16 is identical to that shown in FIGS. 1 and 2, with the exception-being that the valve body 1" replaces valve body 1 of FIG. 1. In FIG. 17 there is shown a front view of the valve body 1" which is substantially similar to the valve body 1', disclosed herein. As with the valve bodies 1 and 1', the face 6" of valve body 1" includes a recess or hole 3". The recess 3" may be a cylindrical recess as described above.

Further, as with valve body 1' the valve body 1" includes a raised ring 7", external to and surrounding the recess 3". The raised ring 7" may be directed towards the opening 70 of the cap 17 (FIG. 16) when assembled into the hemostasis cannula (10" of FIG. 16). One important difference between valve 1" and valve body 1' is the addition internal to valve body 1" of of an integrally molded internal ring or doughnut 8" (FIGS. 16 and 18-19A). Internal ring 8" is formed integrally around a portion of the internal perimeter of recess 3", distal from the portion of the recess intersected by the slit. Further a plane drawn through the internal ring 8", parallel to the face 6", would be perpendicular to a plane drawn through the slit 2". The internal ring 8" may be formed adjacent to and at the same level as the face 6" such that the external ring height (ERH), measured to the internal ring face 8a", is equal to the total ring height (TRH), measured to the valve face 6". Alternatively, as shown in FIG. 19A, the internal ring face 8a" of internal ring 8" can be located at a level higher than the level of valve face 6" such that TRH is greater than ERH. Similarly, the ring may be located in the recess 3" such that the ring face 8a" is located at a level below that of the valve body face 6" (TRH less than ERH).

As with valve body 1', valve body 1" is oblong in shape and has a height dimension $H_{2"}$ which is greater than the height dimension $H_1$ of recess 18 of FIG. 2. Therefore, valve body 1" must additionally be compressed in the direction of arrows 8 in order to be received within recess 18. Again, the oblong shape of the disc and the compressive forces in the direction of arrows 8 have been found to enhance the closing force applied to the slit, as well as make the valve body insensitive to variations in slit height and hole depth. Likewise, valve body 1" of FIGS. 17-19A includes a pair of opposing planar faces 6" which are separated by a peripheral edge 5".

Figure 18:
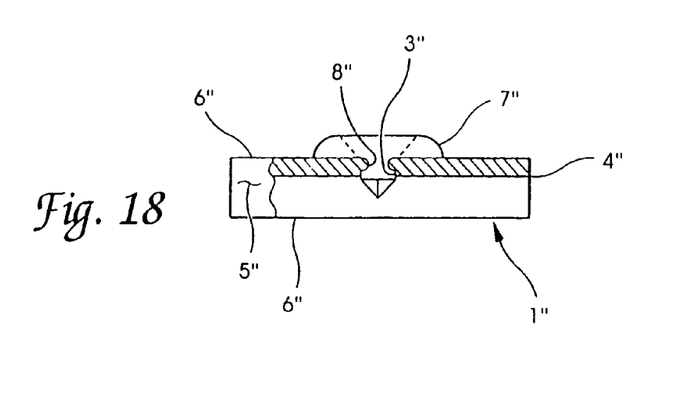
FIG. 18 is a side partially cut-away view of the valve body shown in FIG. 17.
Figure 19:
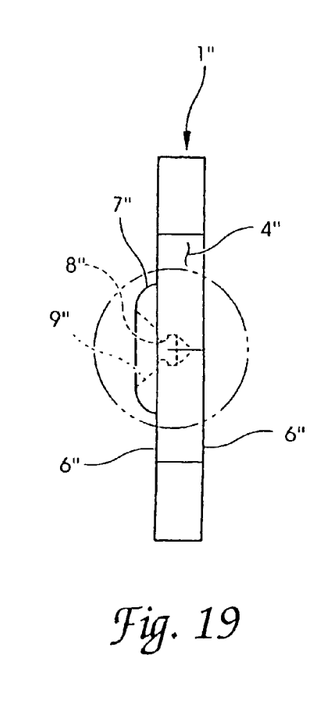
FIG. 19 is a side view of the valve body shown in FIGS. 17 and 18.
Figure 19A:
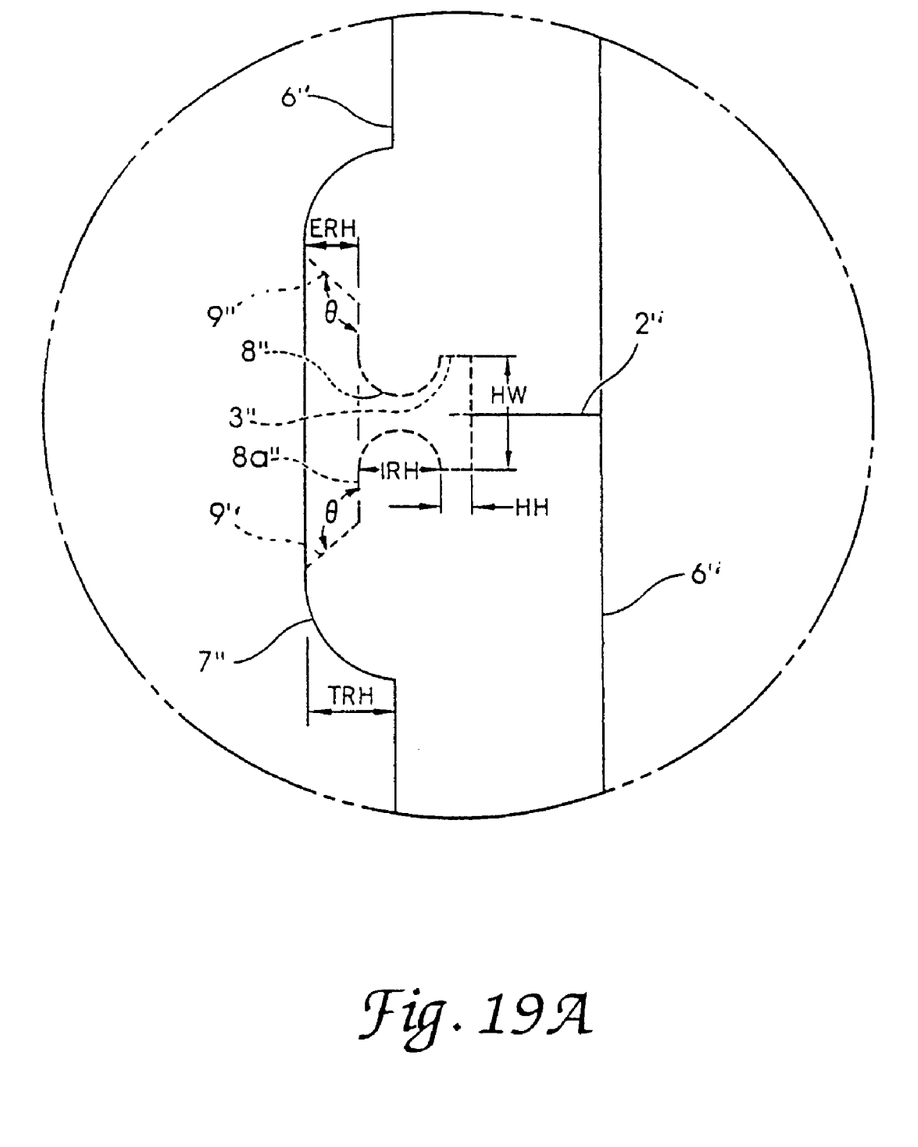
FIG. 19A is an enlarged view of a portion of the valve body shown in FIGS. 17-19.

As noted above, a hole recess 3" is made through one of the faces 6" and extends partially through the valve body as shown in FIG. 18. The hole 3" may be formed by molding during the process of forming the disk or punched, cut or drilled in a separate operation. In one preferred embodiment, the hole 3" and the internal ring 8" are formed integrally using a pin which has been modified to form the cylindrical recess in the face 6" of the valve body 1". The modification is achieved by grinding a groove in the aforementioned pin. In one preferred embodiment, the pin groove was cut to have a radius of about 0.020 inches. Thus, the pin portion is used to form the recess 3", while the groove forms the internal ring 8". The internal ring 8" has been added to prevent leaking through the valve body 1" when small diameter devices (such as small diameter wire guides, etc.) are used. The internal ring 8" offers an improvement over the valve body designs of valve bodies 1 and 1' when used with small diameter devices. For example, the internal ring 8" has been found to provide a better seal around guide wires in the range of 0.018" to 0.038". However, tests have shown an increase of sealing efficiency over valve bodies having a recess but no internal ring with all devices put through the valve.

As with the valve body 1', a slit 2" is made through the other face 6", opposite to the face 6" bearing the recess 3" therethrough. The slit 2" extends partially through the valve body 1" intersecting hole 3" within the valve body 1". Likewise, the raised ring 7" on the top surface of the valve provides a lead-in to the hole 3" of the valve body 1". As such, the raised ring 7" makes it easier to place very small diameter devices through the valve, while the internal ring 8" provides for a tighter seal around those devices. The extra material externally surrounding the hole 3" additionally makes the valve less likely to tear. The internal ring 8" additionally imparts some degree of tear propagation resistance for tears emanating from the slit.

Further, valve body 1" (including raised ring 7' and internal ring 8") is preferably made from silicon rubber or another elastomer having a Durometer hardness (Shore A scale) anywhere between 20A and 90A. Evaluations were conducted on valve bodies differing in Durometer (Shore A scale from 29A to 51A) and diameter. Other physical characteristics measured were weight and thickness. Insertion force measurements and leakage were then conducted on the valves after they were built up in cap and body assembly. The optimal scenario was determined to be where the insertion force (measured by the amount of force needed to insert an 8 Fr. dilator across the valve at a constant rate) is low, and the leakage nonexistent. An Analysis of Variance was conducted on the physical characteristics, and it was found that the most statistically significant factor effecting the insertion force was Durometer. It was found that the higher the Shore A Scale number, the greater was the insertion force.

Experimentally, the Miles-Mobay 30 Durometer material exhibited the lowest insertion force measured. Although the 30 Durometer material seem to be the most preferred hardness for the present invention, Durometers in enhanced tear resistant material from 25A to 50A would additionally make practical valves, such as valve bodies 1, 1' and 1".

Referring now to FIGS. 17-19A, valve body 1" preferably has an oblong shape such that peripheral edge 5" includes a pair of parallel planar surfaces 4" which are perpendicular to the plane defined by slit 2". Slit 2" preferably extends completely across one of the faces 6" and extends into the valve body to a depth of between ⅓ and ⅔ the thickness of the valve body.

In one particular embodiment of the present invention, the thickness of the valve body 1" may be 0.062 inches +/−0.002 inches and the slit depth may be between 0.040 and 0.045 inches. Hole 3" preferably has a diameter of between 0.010 and 0.035 inches and, like slit 2", has a depth preferably between ⅓ and ⅔ the thickness of valve body 1". The combined depth of hole 3" and slit 2" must be sufficient that they intersect within the valve body and create an opening completely through the valve body for receiving a catheter or the like therethrough. In one particular embodiment the overlap between the valve body and the slit was 0.007 inches. Of course, the oblong shape of valve body 1" results in it having a height dimension $H_{2"}$ which is greater than its width dimension $W_{2"}$. In the above mentioned particular embodiment, height $H_{2"}$ is between 0.405 and 0.410 inches in diameter compared to a width $W_{2"}$ of between 0.340 and 0.360 inches.

In the present embodiment, the raised ring 7" is centered around the hole 3". Additionally, as can be seen more clearly in FIG. 19A, the inner wall 9" of the raised ring 7" is sloped from the top of the raised ring 7" down to the face 8a" of the internal ring 8". An angle θ can be measured between a plane parallel to the face 8a" and the inner wall 9". In the above mentioned particular embodiment angle θ is 45 degrees.

Further, for the purposes of example only, the dimensions of one particular valve body of the type described in connection with the embodiment of FIGS. 17-19A will be given. Note that these dimensions are given as example only and are not meant to limit the present invention only to valve bodies having those dimensions listed herebelow. In the one particular example described in this paragraph, the outer diameter of raised ring 7" was chosen to be between 0.145-0.155 inches, preferably 0.150 inches, while the inner diameter, measured at the top of the raised ring, may be between 0.080-0.095 inches in diameter. Additionally, the raised ring may extend between 0.25 and 0.030 inches above the face 6" (TRH=between 0.25 and 0.030 inches). In this particular example the height (ERH) from the top of the external ring 7" to the face of the internal ring 8a" is 0.016 inches. In this same particularly described example the internal ring height (IRH) was chosen to be 0.021 inches.

Further in this example, the internal diameter (I.D.) of the internal ring 8" in one embodiment is 0.016 inches before it is put in the cap and body. After being constrained by the cap and body (and resultingly compressed in the direction of arrows 8 in FIG. 2, perpendicular to the slit 2") the I.D. becomes oval and measures 0.013 inches by 0.017 inches due to the compressive effects of the cap on the oblong disc.

Additionally in this particular example, the diameter of the recess 3" was chosen to be between 0.030 inches and 0.040 inches, more particularly the diameter was chosen to be 0.036 inches. Additionally, the hole height (HH) measured from the base of the hole 3" to the proximal surface of the ring 8" is 0.016 inches in the particularly described embodiment. The hole width HW of the hole 3" in that particularly described example was 0.036 inches. Further, in the present example, the recess 3" and the slit 2" overlap by 0.007 inches.

As can be further seen in FIG. 19A, in the preferred embodiment, the tapered walls terminate at the surface of the internal ring face 8a" prior to the beginning of the hole 3", thus forming a small planar surface between the hole 3" and the raised ring 7". Alternately, the sloping inner wall 9" can terminate directly at the end of the ring face 8a", at the lead in to the hole 3".

As with the previous embodiments of the invention, before being compressed, valve body 1" has a height dimension $H_{2"}$ which is greater than height dimension $H_1$ of recess 18 shown in FIGS. 1 and 2. So that the compression forces on valve body 1" are directed only perpendicularly to slit 2", valve body 1" has a width dimension $W_{2"}$ which is less than the width dimension $W_{1"}$ of recess 18 of FIG. 1, which, as noted above, will provide a greater closing force to the slit when the valve is compressed in the cannula cap and body assembly. Planar portions 4" allow valve body 1" to expand in its width dimension without interacting with the recess when it is compressed and received within the recess 18 of FIG. 1.

The compression applied to the valve body could be produced by any of a number of methods. The recess in the housing could be shaped so that it applied the needed pressure to produce a closing force to the opening in the valve body. The closing force produced by the compression on the opening through the valve body improves the performance of most if not all of the valve bodies of the prior art as well as those in accordance with FIGS. 5-8, 13-15A and 17-19A. It has been found that valve bodies 1, 1' and 1" work well with a wide range of device diameters, and because of the compression, the valve body is insensitive to such factors as slit depth and hole diameter.

Figure 4:
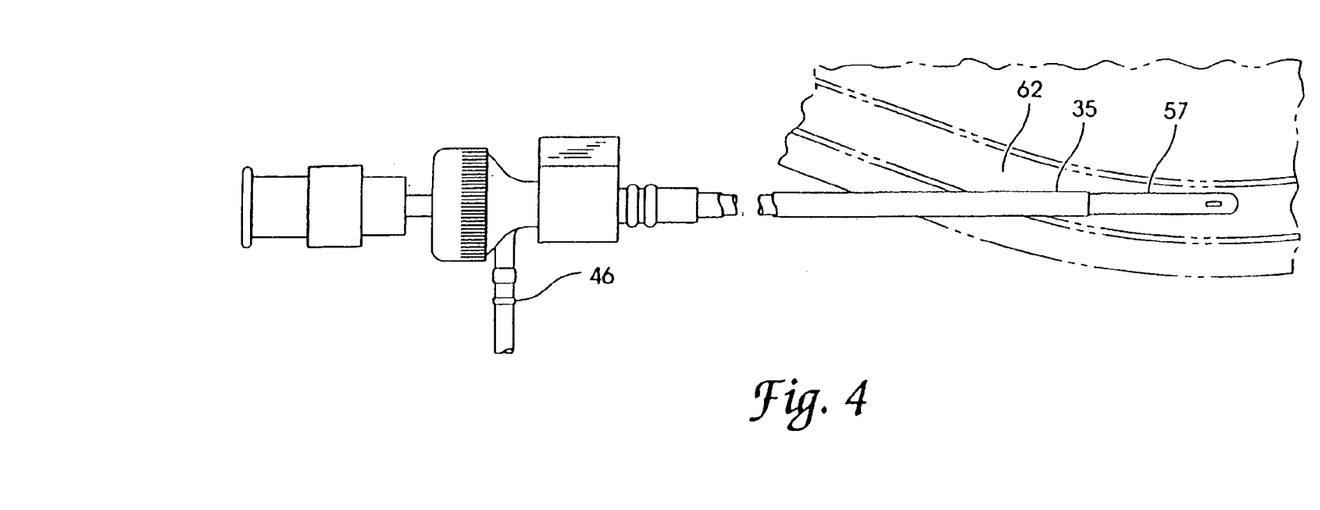
FIG. 4 is a view similar to FIG. 3 showing the cannula in position in the lumen of a blood vessel with a catheter enclosed therein.
Figure 5:
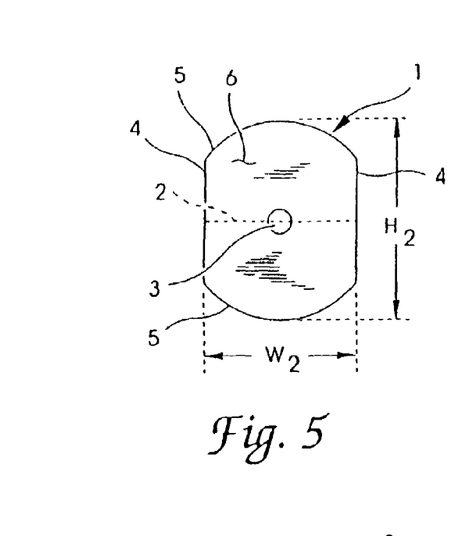
FIG. 5 is a front view of the valve body used in the hemostasis cannula of FIGS. 1 and 2.
Figure 6:
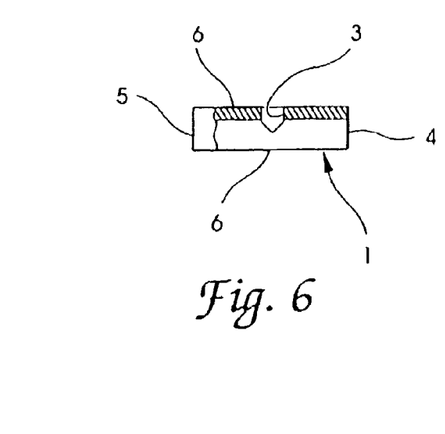
FIG. 6 is a side partially cut-away view of the valve body shown in FIG. 5.

In operation as shown in FIGS. 3 and 4, a hollow needle subcutaneously enters the blood vessel. When the lumen 62 of the vessel has been penetrated, guide wire 61 is threaded into the needle and blood vessel, and the needle is removed. A hollow plastic dilator 56 is then passed through passage 11 of the housing member 12 and is slid over guide 61. The physician then dilates the hole through the vessel wall by maneuvering the tapered end 60 of the dilator 56, and introduces the entrance tube 35 into vessel lumen 62. It should be noted that the outer diameter of the dilator at its constant diameter portion is close to the outer diameter of the flexible tubing 35 so that tubing 35 is guided through the wall of the vessel by the dilator. The cannula is then taped into position on the body of the patient. With the feed tube 46 fastened to projection 47, and while maintaining a slow flow of heparin saline solution into passage 11 through the tube 46, the physician withdraws dilator 56 and guide 61. At this point, slit 2, 2' or 2" in valve body 1, 1' or 1", respectively, closes. The closure of slit 2, 2' or 2" insures that no air passes through the opening 70 of cap 17 and through valve body 1, 1' or 1" into passage 11. Thus, the present device not only prevents blood loss but also insures against the possibility of an air embolism.

The catheter 57 is then Introduced through the opening in cap 17 and passes through valve body 1, 1' or 1". Catheter 57 is guided through passage 11 and flexible tubing 35 by the tapered surfaces 71 and 72. The catheter finally passes into lumen 62 of the blood vessel. Hole 3, 3' or 3" (and in the case of valve bodies 1' and 1", raised rings 7' and 7" and further in the case of valve body 1", internal ring 8") forms a seal around the exterior wail of catheter 57 and prevents blood loss through hole 70 in the cap. Passage 11 is constantly flushed by a flow of heparin saline solution introduced through the port 45 and tubing 46 in order to prevent clotting. When catheter 57 has been maneuvered into position, radiopaque fluid is injected through the catheter and X-ray photographs may be taken of the radiopaque configuration of the organ being studied.

When multiple studies are indicated, or if a catheter has not been positioned correctly, the catheter may be easily removed from the cannula housing and replaced with another catheter. Also, a guide wire may be used by passing it through the cannula housing if needed. Because slit 2, 2' or 2" in valve body 1, 1' or 1" closes at the time of removal of the catheter, no bleeding is experienced by the patient and no air is allowed to enter into the patient's blood vessel in the event that the pressure external of the cannula is greater than the pressure within the blood vessel.

While the invention has been illustrated and described in detail in the drawings and foregoing description, the same is to be considered as illustrative and not restrictive in character. For example, the recess in the cannula housing can have various shapes so long as the valve body is of a corresponding cooperating shape to provide compression force in an appropriate direction tending to close the opening in the valve body. It is to be understood that only the preferred embodiments have been shown and described and that all changes and modifications that come within the spirit of the invention are desired to be protected.

What is claimed is:

1. A medical instrument comprising:
   a housing member having a passage through which a catheter including an outer profile is received;
   a cap having a recess formed therein and in fluid communication with the passage, the recess being defined by a first height dimension and a first width dimension, both dimensions across the center of the recess; and
   a valve body to be received in the recess and abut the housing member at an end of the passage to seal the passage, the valve body having first and second faces and a peripheral edge separating the faces, the peripheral edge being non-circular when the valve body is unstressed, the valve body further having a first slit formed on one of the faces and a second slit formed on the other face, each slit formed through a portion of the valve body and intersecting with the other slit within the valve body,
   the valve body conforming to the outer profile of the catheter when the catheter is disposed through the first and second slits to maintain a fluid tight seal between the valve body and the catheter,
   the valve body having a second height dimension and a second width dimension, both dimensions across the center of the valve body, the second width dimension being less than the second height dimension when the valve body is unstressed, the second height dimension being greater than the first height dimension of the recess and the second width dimension being less than the first width dimension of the recess, the second height and the second width dimensions defining a plane parallel to the first and second faces and perpendicular to the slits, the valve body configured to be compressed only along the entire peripheral edge parallel to the second height dimension when the valve body is received by the recess, defining a generally circular shape.

2. The instrument of claim 1 wherein the first and second slits are oriented at an angle with respect to each other.

3. The instrument of claim 1 wherein the first and second slits are perpendicular to each other.

4. The instrument of claim 1 wherein the recess is a circular recess with a circular cross section.

5. The instrument of claim 4 wherein the peripheral edge has an oval shape when the valve body is unstressed before being received in the recess.

6. A medical instrument comprising:
   a housing member having a passage through which a catheter including an outer profile is received;
   a cap having a recess formed therein and in fluid communication with the passage, the recess being defined by a first height dimension and a first width dimension, both dimensions across the center of the recess; and
   a valve body to be received in the recess and abut the housing member at an end of the passage to seal the passage, the valve body having first and second faces and a peripheral edge separating the faces, the peripheral edge being non-circular when the valve body is unstressed, the valve body further having a slit defining a slit plane extending from the first face and partly through the valve body and an opening extending from the second face and partly through the valve body, the slit plane and the opening intersecting within the valve body, the opening provided with an internal ring positioned within the valve body between the second face and the intersection between the slit plane and the opening,
   the valve body conforming to the outer profile of the catheter when the catheter is disposed through the slit plane and the internal ring to maintain a fluid tight seal between the valve body and the catheter,
   the valve body having a second height dimension and a second width dimension, both dimensions across the center of the valve body, the second width dimension being less than the second height dimension when the valve body is unstressed, the second height dimension being greater than the first height dimension of the recess and the second width dimension being less than the first width dimension of the recess, the second height and the second width dimensions defining a plane parallel to the first and second faces and perpendicular to the slit, the valve body configured to be compressed only along the peripheral edge parallel to the second height dimension when the valve body is received by the recess, defining a generally circular shape.

7. The instrument of claim 6 wherein the recess is a circular recess with a circular cross section.

8. The instrument of claim 6 wherein the valve body includes an external raised ring on the second planar face, the external raised ring surrounding the opening.

9. A medical instrument comprising:
   a housing member having a passage through which a catheter including an outer profile is received;
   a cap having a recess formed therein and in fluid communication with the passage, the recess having a first height dimension across the recess; and
   a valve body to be received in the recess and abut the housing member at an end of the passage to seal the passage, the valve body having first and second faces and a peripheral edge separating the faces, the peripheral edge being non-circular when the valve body is unstressed, the valve body further having a first slit formed on one of the faces and a second slit formed on the other face, each slit formed through a portion of the valve body and intersecting with the other slit within the valve body,
   the valve body conforming to the outer profile of the catheter when the catheter is disposed through the first and second slits to maintain a fluid tight seal between the valve body and the catheter,
   the valve body having an oblong shape such that the peripheral edge includes a pair of parallel planar surfaces perpendicular to at least one of the slits, the oblong shape defined by a second height dimension across the center of the valve body and a width dimension across the center of the valve body, the width dimension being less than the second height dimension and parallel to the planar surfaces and the second height dimension being greater than the first height dimension of the recess when the valve body is unstressed, the second height dimension and the width dimension defining a plane parallel to the first and second faces and perpendicular to the slits, wherein the valve body is configured to be compressed only along the entire peripheral edge parallel to the second height dimension producing a closing force on the entire length of one of the slits after removal of the catheter to prevent leakage, and wherein the planar surfaces allow the valve body to expand in the width dimension without interacting with the recess when the valve body is received by the recess, defining a generally circular shape.

10. The instrument of claim 9 wherein the recess is a circular recess with a circular cross section.

11. The instrument of claim 10 wherein the peripheral edge has an oval shape when the valve body is unstressed before being received in the recess.

12. The instrument of claim 9 wherein the first and second slits are oriented at an angle with respect to each other.

13. The instrument of claim 9 wherein the first and second slits are perpendicular to each other.

* * * * *